United States Patent [19]

Arvidson et al.

[11] Patent Number: 4,886,504

[45] Date of Patent: Dec. 12, 1989

[54] RESERVOIR/DISPENSING CONTAINER

[75] Inventors: Russell A. Arvidson, Mundelein, Ill.; James T. Renick, Bristol, Wis.; Robert D. Clegg, Pickerington; Lawrence E. Zimmer, Dublin, both of Ohio

[73] Assignee: Abbott Laboratories, Abbott Park, Ill.

[21] Appl. No.: 122,980

[22] Filed: Nov. 19, 1987

[51] Int. Cl.$^4$ .............................................. A61M 5/185

[52] U.S. Cl. ........................................ 604/257; 604/403

[58] Field of Search ........................... 604/80, 257–261, 604/403

[56] References Cited

U.S. PATENT DOCUMENTS

| | | | |
|---|---|---|---|
| 1,017,773 | 2/1912 | Leach | 604/257 |
| 1,253,955 | 1/1918 | Galligan | 604/257 |
| 3,921,630 | 11/1975 | McPee | 604/257 |
| 3,923,062 | 12/1975 | St. Amand et al. | 604/403 |
| 4,713,064 | 12/1987 | Bruno et al. | 604/257 |

*Primary Examiner*—Max Hindenburg
*Attorney, Agent, or Firm*—Donald O. Nickey; Cliff Dean; Martin Katz

[57] ABSTRACT

A reservoir/dispensing container for use at a patient's bedside for administering nutrients, medicaments, etc. through enteral, I.V. or like systems wherein the container, which is semi-rigid and has nestable stacking means provided thereon, has discharge port means at one end thereof and a fill opening located in a beveled corner wall surface adjacent the end opposite from the discharge port means whereby the container can be filled either while supported in an upright use position, as at a patient's bedside, or while supported on its side with the fill opening facing generally upwardly, as for instance, at a nursing station or in a hospital pharmacy. An adaptor having a reduced-thickness intermediate section is provided for connecting a feeding tube or the like to the discharge port means of the container in a manner preventing kinking of the feeding tube or the like.

3 Claims, 3 Drawing Sheets

RESERVOIR/DISPENSING CONTAINER

BACKGROUND OF THE INVENTION

The present invention relates to a reservoir container for dispensing nutrients, medicaments, etc. to a patient through an enteral, I.V. or like system. Many containers currently in use for such purposes are flexible plastic bags which are not free-standing and thus are quite difficult to not only initially fill but also to refill when necessary without interrupting flow to the patient. At least two hands are needed. Such flexible plastic bags, when filled, are also very difficult to stack, as for storage or during transport. Those bags with plastic tubing pre attached to the discharge port means thereof must also be provided, when packaged prior to use, with quite elaborate and costly means for preventing kinking of the tubing beyond its critical radius.

SUMMARY OF THE INVENTION

The present invention is a new and novel semi-rigid, generally rectangular plastic reservoir container for dispensing nutrients, medicaments, etc. at a patient's bedside. This container has a hanger provided on one end for hanging it from a hook or other support adjacent a patient's bedside and discharge port means at the opposite end to which a feeding tube or the like is to be connected. A special adaptor is provided for connecting a feeding tube or the like to the discharge port means in a manner which prevents kinking of the tubing past its critical point. The container has four side walls, two of which may be narrower than the other two, and a beveled corner wall which extends between one of the narrower side walls and the hanger end of the container at an angle of approximately 45° . A fill opening having a removable closure is provided in the beveled corner wall whereby the fill opening faces upwardly at an approximate angle of 45° both when the container is supported in an upright use position or when it is supported in one of its "lying on its side" positions. Thus, the container may be easily filled or refilled either while it is supported from its hanger in an upright dispensing position, without interrupting flow to the patient, or when the container is free-standingly supported on its narrow side opposite the narrow side which is adjacent the beveled corner wall whereby the fill opening faces generally upwardly. The container may, therefore, be easily filled, using only one hand, while supported on a counter top or other generally level surface, as in a hospital pharmacy, or filled or refilled in the same manner, as at a nursing station. By providing interfitting raised ribbing and mating depressions on the opposing wider sides of the container, a plurality of such containers may be stabilizingly stacked or nested for either storage or transport. This, of course, may not be done with the more commonly used flexible and floppy pre filled dispensing bags. Support feet may be molded into the narrow supporting side of the container for additional stability thereof. A unique adaptor is provided to prevent undesirable kinking of a tubing which is to be connected to a discharge port means of the container.

DESCRIPTION OF THE PREFERRED EMBODIMENT

Figure 1:
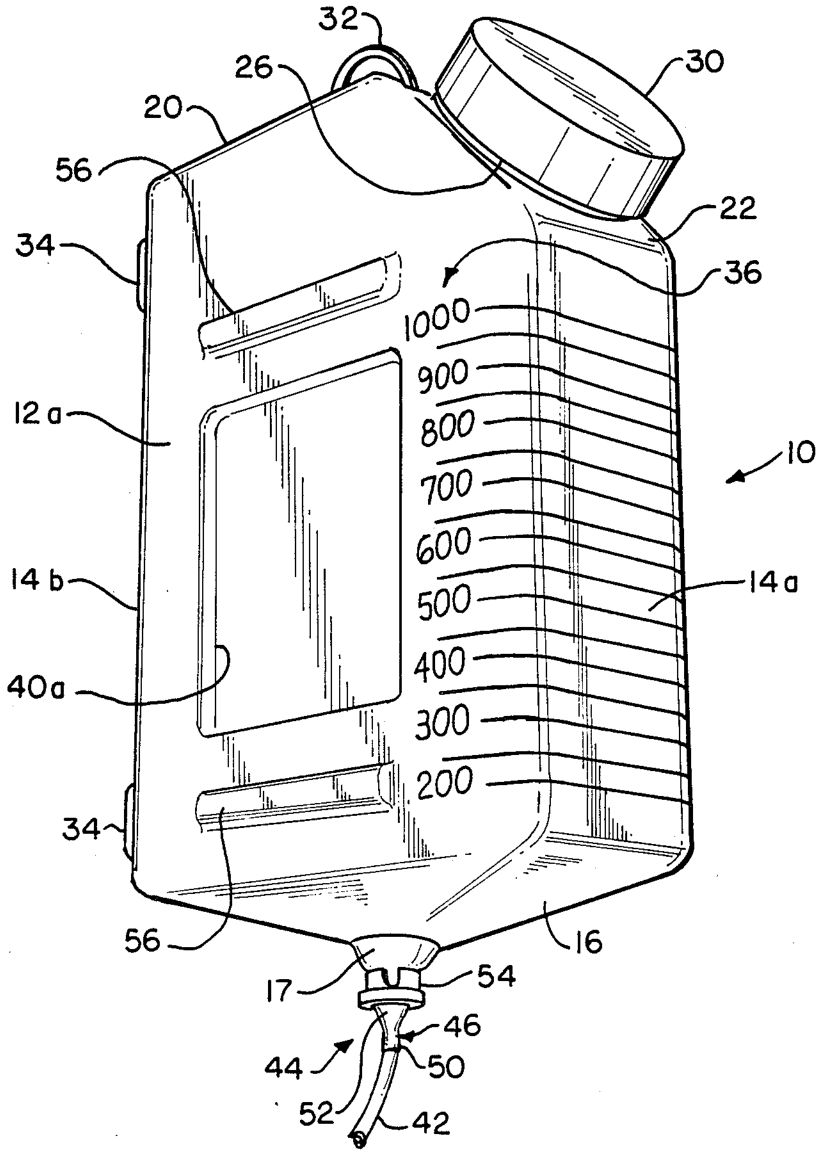
FIG. 1 is a front perspective view of a reservoir/dispensing container embodying the invention when disposed in its upright dispensing position.
Figure 2:
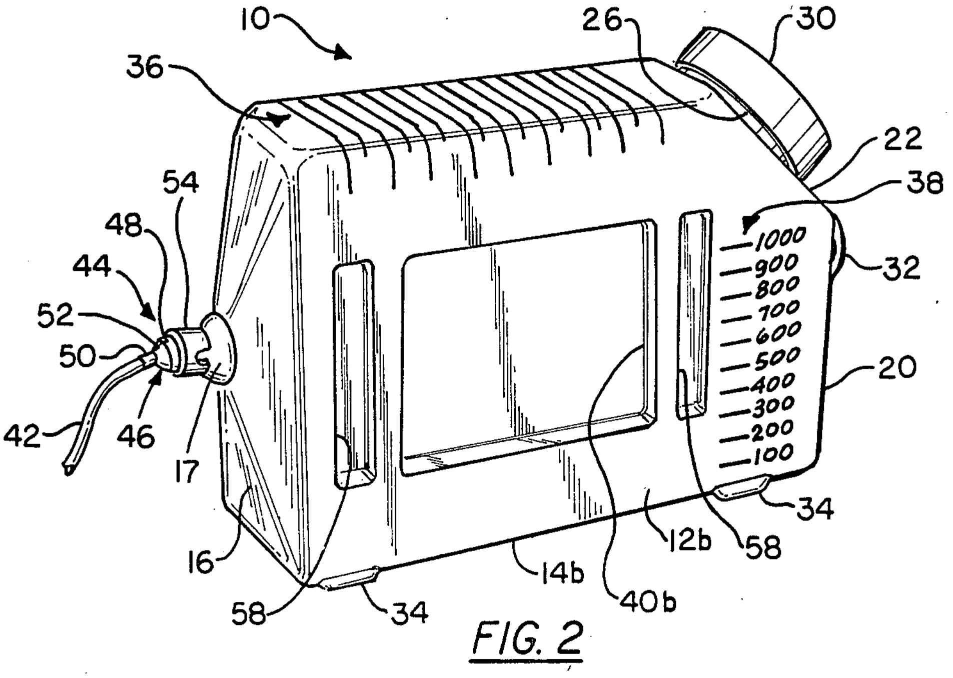
FIG. 2 is a rear perspective view of the reservoir/dispensing container of FIG. 1 when disposed in its "lying on its side" filling position.
Figure 8:
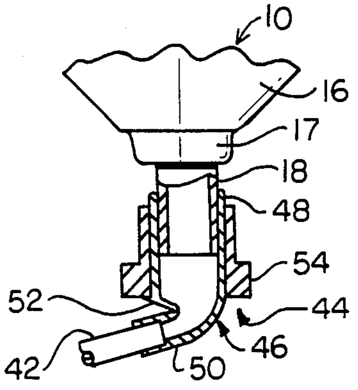
FIG. 8 is a partial elevational view of the discharge end of the container and shown partially in vertical section to illustrate how the adaptor prevents kinking of a feed tube or the like connected to the discharge port means of the container when a lateral force is applied thereto.

Referring now to the drawings, a preferred form of a reservoir/dispensing container 10 embodying the invention is shown in FIG. 1 in its upright dispensing position and in FIG. 2 in its "lying on its side" filling position. The container 10 , which is semi-rigid and formed of a suitable food grade plastic such as polyethylene, is generally rectangular in configuration with a pair of opposing sidewalls, front wall **12*a* and rear wall 12*b*, and a pair of opposing end walls, right end wall 14*a* and left end wall 14*b*, which are relatively narrower than the sidewalls 12*a* and 12*b*. A bottom wall 16, as viewed when the container 10 is disposed in its upright dispensing position (FIGS. 1, 3, 5 and 6), is gently tapered downwardly from the side and end walls 12*a*, 12*b*, 14*a*and 14*b* toward a centered well formation 17 thereof which is provided with discharge port means in the form of an open spigot 18, as shown in FIG. 8**.

At the opposite end of the container 10 there is provided a relatively horizontally disposed top wall 20 and, between the right end of the top wall 20 and the upper end of the right end wall **14*a*, a beveled or inclined corner wall 22 is provided which is preferably disposed at an angle of approximately 45° to both the top wall 20 and the right end wall 14*a***.

A fill opening 24 defined by an outwardly projecting neck portion 26 is provided in the beveled corner wall 22 whereby the fill opening 24 faces upwardly at a 45° angle both when the container 10 is supported in its upright dispensing position, as at a patient's bedside (FIG. 1) , and in a "lying on its side" position on its left end wall **14*b*, as when supported on a level surface as in a hospital pharmacy or at a nursing station (FIG. 2) , the latter position being disposed at an angle of approximately 90° to the upright dispensing position. The neck portion 26 is threaded, as at 28, for receiving a removable threaded closure or cap 30**.

The top wall 20 is provided with a hanger 32 for supporting the container from a hook, pole, or other suitable supporting means at a patient's bedside. Further, as shown in FIGS. 1, 2, 3 and 6, the left end wall **14*b* preferably has a pair of spaced apart, supporting feet formations 34 molded thereon to better stabilize the container 10** when supported in its "lying on its side" filling position.

The container 10, when supported on its "lying on its side" position, may be very easily filled or refilled, using only one hand if necessary, when supported on a level surface, as in a hospital pharmacy or at a nursing station. Further, the container 10 may also be just as easily refilled while in its upright use position at a patient's bedside without having to interrupt flow to the patient.

As shown in FIGS. 1 and 2, two separate measurement indicia 36 and 38 may be provided on the see-through plastic container 10 to provide an indication of the volume of nutrient, medicament, etc. in the container 10. Recesses 40a and 40b may be provided in the front and rear sidewalls 12a and 12b to receive labels bearing patient, medicament, etc. information.

Figure 7:
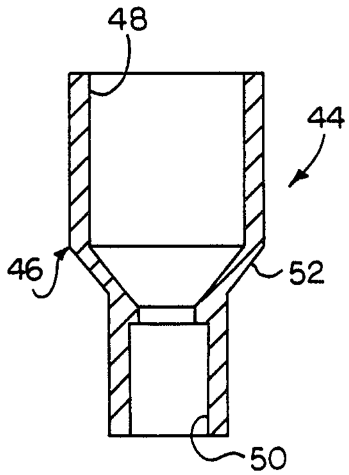
FIG. 7 is an enlarged vertical sectional view through the adaptor shown in FIGS. 1–3, 5 and 6.

Often, a flexible plastic feeding tube or the like 42 is prefitted to the discharge spigot 18 of the container 10 and when the container/tube assembly is packaged prior to use, the tube is kinked beyond its critical angle which may result in problems during use. To eliminate this problem, an adaptor 44 is provided between the discharge spigot 18 and the tube 42. The adaptor 44, as best shown in FIGS. 7 and 8, is in the form of a flexible plastic sleeve 46 having a first bored end section 48 which is sealingly fitted over the discharge spigot 18 and a second bored end section 50 into which an end of the tube 42 is sealingly inserted. An intermediate section 52 between the two end sections 48 and 50 has a thinner wall thickness whereby when a lateral force is applied thereto, as may happen when the container/tube assembly is packaged, the adaptor's intermediate section 52 bends as shown in FIG. 8 without kinking the tube 42. A known type rigid plastic collar 54 may be provided to stabilize mounting of the adaptor 44 on the container discharge spigot 18. As best illustrated in FIG. 7, when the two end sections 48 and 50 of the adaptor 44 are of different diameters, the intermediate section 52 is conical in configuration.

Figure 3:
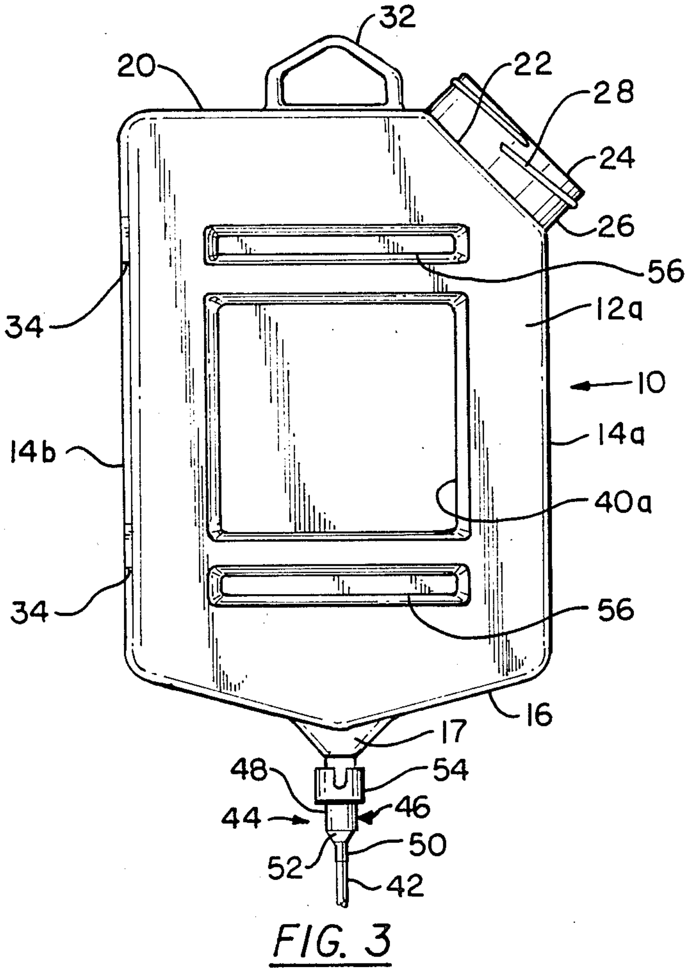
FIG. 3 is a rear elevational view of the container as shown in FIG. 1 with the fill opening closure removed and showing the rear sidewall of the container opposite the front sidewall shown in FIG. 1.
Figure 4:
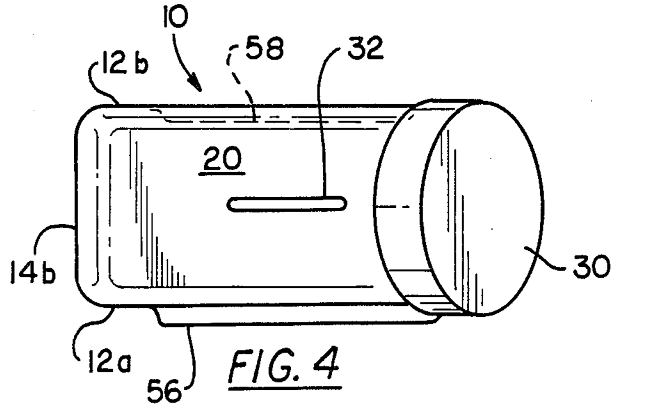
FIG. 4 is a top plan view of the container as shown in FIG. 3 with the fill opening closure assembled thereon.
Figure 5:
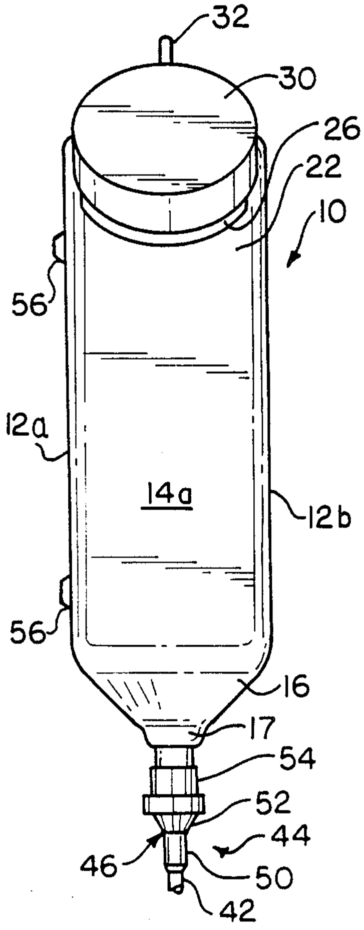
FIG. 5 is a right end elevational view of the container as shown in FIG. 4.
Figure 6:
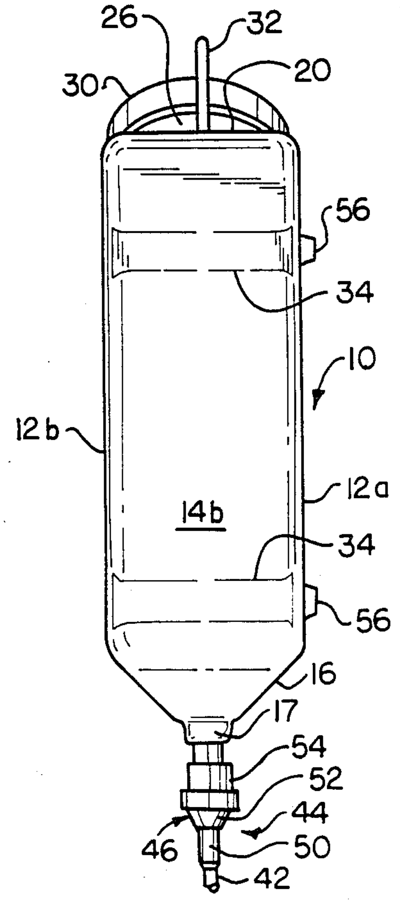
FIG. 6 is a left end elevational view of the container as shown in FIG. 4.

To provide stabilized stacking of empty or pre-filled containers 10, as for storage or during transport thereof, a raised ribbing pattern may be provided on one side wall with a mating pattern of recesses being provided on the opposite side wall. As illustrated in FIGS. 1, 3 and 4, a pair of raised ribs 56 are provided on the front side wall 12a above and below the label recess 40a and, as illustrated in FIGS. 2 and 4, a pair of mating recesses 58 are provided on the rear side wall 12b, above and below the label recess 40b.

While there has been shown and described a preferred embodiment of the invention, it will be obvious to those skilled in the art that changes and modifications may be made without departing from the invention, and it is intended by the appended claims to cover all such changes and modifications as fall within the true spirit and scope of the invention.

What is claimed as new and desired to be secured by Letters Patent of the United States is:

1. A reservoir/dispensing container comprising a semi-rigid, generally rectangular container with four side walls haing discharge port means at one end thereof and means defining a closable fill opening adjacent the opposite end thereof and wherein said fill opening is defined in a beveled wall surface extending between said opposite end and one of said sidewalls, supporting means are provided on the side wall opposite said fill opening to facilitate supporting said container on its side, interengagable stacking means are provided on an opposing pair of said walls to permit stabilized stacking of two or more of said container, said interengagable stacking means being provided by a pattern of raised projections and/or ribs with the opposite side wall being provided with an identical pattern of depressions and/or grooves, adaptor means for connecting a feed tube or the like to said discharge port means, said adapter comprising a sleeve-like member having a first bored section at one end for sealed connection to said container discharge port means, a second bored section having a lesser diameter than said first bored section at the opposite end sealingly receiving an end of said tube and a flexible reduced thickness section intermediate said bored end sections which is conical in configuration whereby said intermediate adaptor section, rather than said tube, flexes upon application of a lateral force thereto.

2. A container as recited in claim 1 wherein hanger means are provided on said opposite end of said container to facilitate supporting said container in said upright dispensing position.

3. A container as recited in claim 1 wherein said multi-sided container is rectangular and is characterized by two sides which are narrower than the other two relatively wider sides.

* * * * *